(12) United States Patent
Scholten et al.

(10) Patent No.: US 8,377,315 B2
(45) Date of Patent: Feb. 19, 2013

(54) METHOD FOR MANUFACTURING POROUS MICROSTRUCTURES, POROUS MICROSTRUCTURES MANUFACTURED ACCORDING TO THIS METHOD, AND THE USE THEREOF

(75) Inventors: Dick Scholten, Stuttgart (DE); Tjalf Pirk, Stuttgart (DE); Michael Stumber, Korntal-Muenchingen (DE); Franz Laermer, Weil der Stadt (DE); Ralf Reichenbach, Esslingen (DE); Ando Feyh, Tamm (DE)

(73) Assignee: Robert Bosch GmbH, Stuttgart (DE)

( * ) Notice: Subject to any disclaimer, the term of this patent is extended or adjusted under 35 U.S.C. 154(b) by 328 days.

(21) Appl. No.: 12/810,973

(22) PCT Filed: Nov. 19, 2008

(86) PCT No.: PCT/EP2008/065806
§ 371 (c)(1),
(2), (4) Date: Sep. 24, 2010

(87) PCT Pub. No.: WO2009/086986
PCT Pub. Date: Jul. 16, 2009

(65) Prior Publication Data
US 2011/0281102 A1    Nov. 17, 2011

(30) Foreign Application Priority Data
Jan. 8, 2008 (DE) .......... 10 2008 003 453

(51) Int. Cl.
*C23F 1/00* (2006.01)
(52) U.S. Cl. .......... 216/2; 216/56; 216/63; 216/67
(58) Field of Classification Search .......... None
See application file for complete search history.

(56) References Cited

U.S. PATENT DOCUMENTS

| | | | | |
|---|---|---|---|---|
| 3,962,052 A | * | 6/1976 | Abbas et al. | 216/2 |
| 5,342,478 A | * | 8/1994 | Welbourn | 216/24 |
| 5,750,000 A | * | 5/1998 | Yonehara et al. | 438/459 |
| 6,127,281 A | * | 10/2000 | Sakaguchi et al. | 438/747 |
| 2012/0058328 A1 | * | 3/2012 | Tourvieille et al. | 428/315.7 |

FOREIGN PATENT DOCUMENTS
DE    102006028916    12/2007

OTHER PUBLICATIONS

International Search Report, PCT International Patent Application No. PCT/EP2008/065806, dated Nov. 2, 2009.
Cohen M.H., et al: "Microfabrication of Silicon-Based Nanoporous Particulates for Medical Applications" Biomedical Microdevices 5:3, 253-259, Sep. 30, 2003, Klumer Academic Publishers, XP002551837.

* cited by examiner

*Primary Examiner* — Duy Deo
(74) *Attorney, Agent, or Firm* — Kenyon & Kenyon LLP

(57) ABSTRACT

A method for manufacturing porous microstructures in a silicon semiconductor substrate, porous microstructures manufactured according to this method, and the use thereof.

17 Claims, 2 Drawing Sheets

METHOD FOR MANUFACTURING POROUS MICROSTRUCTURES, POROUS MICROSTRUCTURES MANUFACTURED ACCORDING TO THIS METHOD, AND THE USE THEREOF

FIELD OF THE INVENTION

The present invention relates to a method for manufacturing porous microstructures, porous microstructures manufactured according to this method, and the use thereof.

BACKGROUND INFORMATION

Porous silicon has numerous possible uses in medicine due to a large internal surface, for example as a reservoir for the release of medications. Electrochemically manufactured porous silicon is typically used, a porous, spongy structure being produced in the silicon, for example in the area of the surface of a silicon wafer.

Conventionally, porous silicon particles are manufactured according to the method in which, for example, a large-area porous layer is produced on a silicon wafer, for example, this layer being detached by mechanical action, and the particles are separated by mechanical disintegration of the porous material, for example, by grinding.

Particles having undetermined size distribution and shape of the individual particles arise through the mechanical disintegration. In addition, the surface of the porous particles is typically greatly damaged or even destroyed by the mechanical action. In addition, the shape of the particles manufactured in this way is typically not reproducible, in particular, reproducible round particles may hardly be manufactured in this way.

SUMMARY

An example method according to the present invention for manufacturing porous microstructures in a silicon semiconductor substrate may have the advantage that porous silicon structures having previously defined shape and size may be manufactured.

This may be achieved according to an example method of the present invention which includes the following steps:
a) applying and structuring a masking layer on the external surface of the front side of a silicon semiconductor substrate, discrete holes having a mean diameter in the range of $\geq 0.1$ μm to $\leq 500$ μm being formed in the masking layer;
b) producing recesses in a silicon semiconductor substrate, the recesses each defining a substructure of the porous microstructures;
c) removing the masking layer;
d) applying and structuring a sacrificial layer, the sacrificial layer having discrete through holes having a diameter in the range of $\geq 0.1$ μm to $\leq 150$ μm, which are each situated centrally in the recesses;
e) applying a silicon layer, the silicon layer filling up the recesses and forming a layer above the sacrificial layer;
f) porosifying the silicon layer;
g) applying and structuring a further masking layer on the porosified silicon layer, the further masking layer covering the areas above the recesses, which form a further substructure of the porous microstructures;
h) anisotropic etching of the porosified silicon layer;
i) removing the further masking layer;
j) removing the sacrificial layer;
k) detaching or separating the porous microstructures.

The term "sacrificial layer" means a layer which is removed again in a later method step.

The term "doping" has the significance in the meaning of the present invention that the doped area or the doped layer has a higher doping than the original area or an adjoining area or layer of the semiconductor substrate. Doping may be performed using boron, for example, in particular, boron may be implanted or a boron glass coating may be performed.

Furthermore, manufacturing round, porous silicon microstructures having diameters from several micrometers up to several hundred micrometers, as well as porous microneedles, is made possible by the method according to the present invention.

A further advantage of the example method according to the present invention may be provided in that the method only has a few method steps. The example method according to the present invention preferably requires no more than three masking levels. This allows the manufacturing of porous microstructures having lower manufacturing costs.

BRIEF DESCRIPTION OF THE DRAWINGS

Exemplary embodiments of the present invention are shown in the drawings and are explained in greater detail below.

DETAILED DESCRIPTION OF EXAMPLE EMBODIMENTS

An example method according to the present invention is first described for exemplary purposes.

A possible manufacturing method of porous microstructures 8 in the form of microneedles is shown in FIGS. 1a through 1f.

Figure 1A:
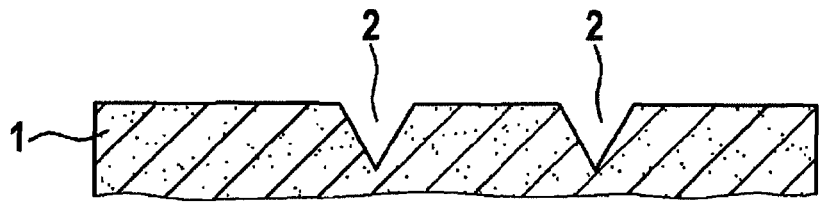
FIGS. 1a through 1f show schematic cross-sectional views of the basic manufacturing steps of porous microstructures in the form of microneedles according to a first specific embodiment of the present invention.

FIG. 1a shows a silicon semiconductor substrate 1, which has recesses 2. To manufacture recesses 2, a masking layer, for example formed from $SiO_2$ or $Si_3N_4$, was applied to the external surface of the front side of silicon semiconductor substrate 1 and structured by photolithography. For this purpose, a photoresist layer, for example AZ® 1529 (AZ Electronic Materials), was applied to the masking material, exposed using a mask, and subsequently removed. The masking layer was subsequently etched using reactive ion etching methods, for example, discrete holes corresponding to the exposure mask being formed in the masking layer.

To produce recesses 2, for example, an etching depth of 20 μm was produced using a self-stopping square mask opening of 28 μm edge length in an aqueous KOH solution at 80° C. Typical etching rates are in the range $\leq 4$ μm/minute. Recesses 2 each define a substructure of porous microstructures 8. The masking layer was subsequently removed.

Figure 1B:
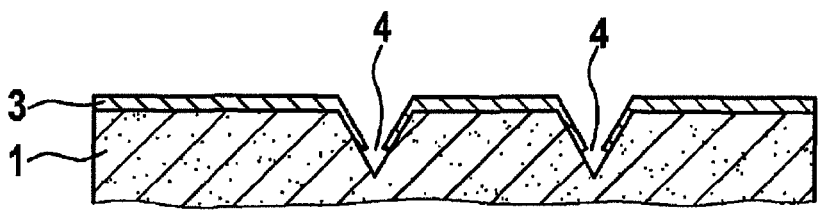

As shown in FIG. 1b, a sacrificial layer 3 was applied to silicon semiconductor substrate 1 having recesses 2. For this purpose, a silicon dioxide layer of a thickness of approximately 1 μm was produced at a temperature of approximately 1100° C., preferably in a moist environment, for 1 to 2 hours through thermal oxidation of silicon semiconductor substrate 1. Sacrificial layer 3 was structured by lithography. Holes 4 situated centrally in recesses 2 in the silicon dioxide layer having a diameter of 8 μm were etched by etching using a buffered hydrofluoric acid solution containing 18.5 vol. % HF, in relation to the total volume of the solution, for 15 minutes at 25° C.

Figure 1C:
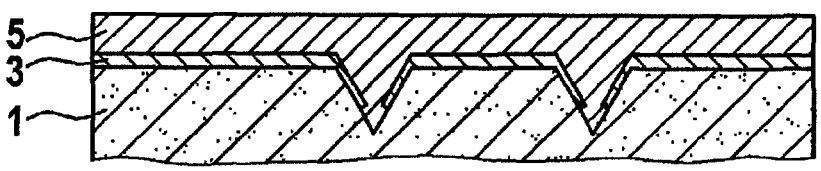
Figure 1D:
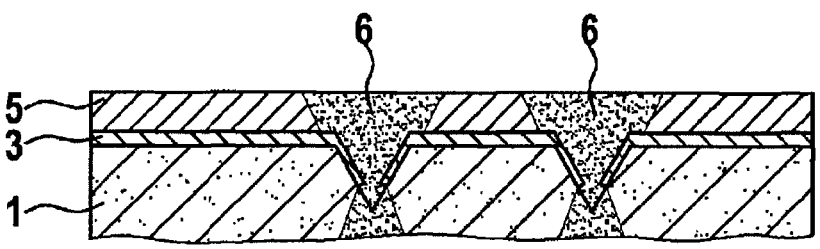

In a following method step, a polycrystalline silicon layer 5 was applied using a PECVD method, as shown in FIG. 1c, for example. Polycrystalline silicon layer 5 had a thickness above the recesses in the range of 0.5 μm to 5 μm. Silicon layer 5 was subsequently p++ doped by implantation of boron, doping having $10^{19}$ charge carriers/cm$^3$ being performed. Doped silicon layer 5 was porosified by electrochemical etching in an electrolyte containing hydrofluoric acid, having a hydrofluoric acid content in the range of 30 vol. % and having a content of isopropanol or ethanol in the range of 10 vol. % to 30 vol. %, in relation to the total volume of the electrolyte, the current density being 100 mA/cm$^2$. In this case, a porosity of 40% to 50% and a pore diameter of 20 nm were produced. The current preferably flowed through holes 4 in sacrificial layer 3, whereby areas 6 in silicon layer 5 above the recesses were preferentially porosified, as shown in FIG. 1d.

Figure 1E:
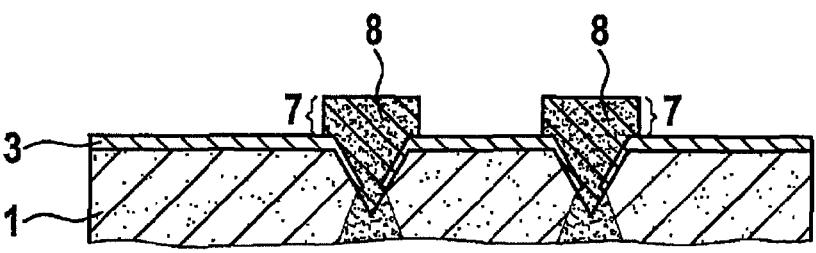

A masking layer, preferably photoresist, was applied to porosified silicon layer 5 and structured by photolithography in a further method step, the masking layer covering the porosified areas of silicon layer 5 above recesses 2. These areas form a further substructure of porous microstructures 8. The structures of porous microstructures 8 were etched out of porosified silicon layer 5 by subsequent anisotropic etching, preferably using DRIE methods, as shown in FIG. 1e. The uncovered areas of silicon layer 5 were removed up to the etch stop on silicon oxide sacrificial layer 3, whereby structures 7 of porous microstructures 8 protruding out of sacrificial layer 3 were formed.

Figure 1F:

Subsequently, sacrificial layer 3 was removed by currentless gas phase etching employing HF vapor. Porous silicon structures 8 were mechanically removed by ultrasound. After the detachment from silicon semiconductor substrate 1, porous microstructures 8 in the form of microneedles were obtained, as shown in FIG. 1f.

As shown in FIGS. 2a through 2f, the method according to the present invention is further usable to produce porous microstructures having rounded shape 8'. Rounded recesses 2' were first produced in a silicon semiconductor substrate 1 by isotropic etching, for example using $ClF_3$.

To manufacture recesses 2', a masking layer, for example formed from $SiO_2$ or $Si_3N_4$, was applied to the external surface of the front side of silicon semiconductor substrate 1 and structured by photolithography. For this purpose, a photoresist layer, for example AZ® 1529 (AZ Electronic Materials), was applied to the masking material, exposed using a mask, and subsequently removed. The masking layer was subsequently etched using reactive ion etching methods, for example, discrete holes corresponding to the exposure mask being formed in the masking layer.

For example, to produce recesses 2' through holes in the masking layer having a diameter of 1 μm, an etching depth of 30 μm was produced at an etching rate of 10 μm/minute in an etching time of 3 minutes using $ClF_3$. This etching process is very isotropic, whereby a semi-round shape may be obtained.

Typical etching rates are in the range $\leq 20$ μm/minute. Recesses 2' each define a substructure of porous microstructures 8'. The masking layer was subsequently removed.

Figure 2A:
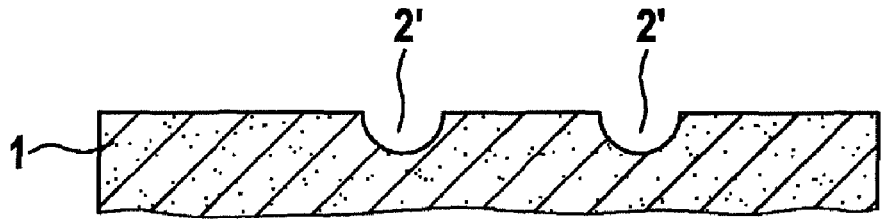
FIGS. 2a through 2f show schematic cross-sectional views of the essential manufacturing steps of rounded porous microstructures according to a second specific embodiment of the present invention.
Figure 2B:
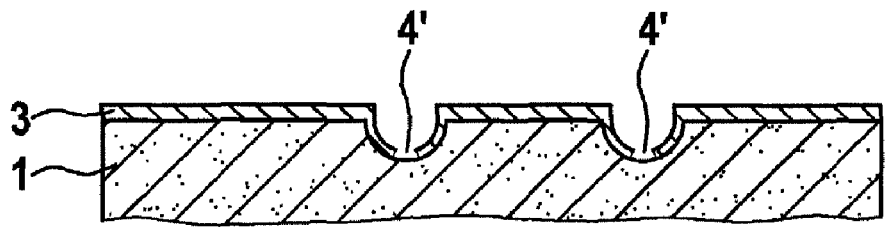

As shown in FIG. 2b, a sacrificial layer 3 was applied to silicon semiconductor substrate 1 having recesses 2'. For this purpose, a silicon dioxide layer of a thickness of approximately 1 μm was produced at a temperature of approximately 1100° C., preferably in a moist environment, for 1 to 2 hours through thermal oxidation of silicon semiconductor substrate 1. Sacrificial layer 3 was structured by lithography. Holes 4' situated centrally in recesses 2' in the silicon dioxide layer having a diameter of 5 μm were etched by etching using a buffered hydrofluoric acid solution containing 18.5 vol. % HF, in relation to the total volume of the solution, for 15 minutes at 25° C.

Figure 2C:
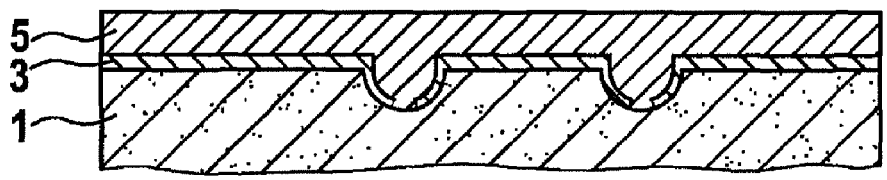
Figure 2D:
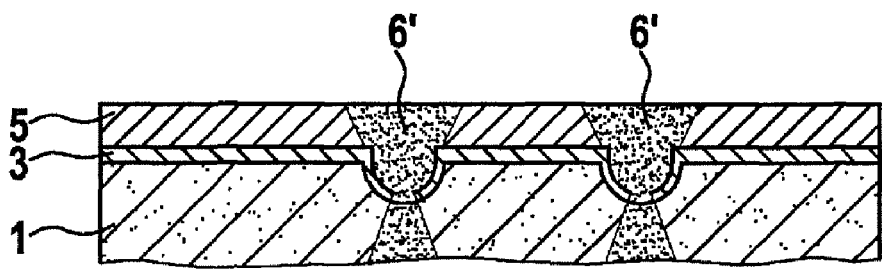

In a following method step, a polycrystalline silicon layer 5 was applied using a PECVD method, as shown in FIG. 2c, for example. Polycrystalline silicon layer 5 had a thickness above the recesses in the range of 0.5 μm to 5 μm. Silicon layer 5 was subsequently p++ doped using implantation of boron, a doping having $10^{19}$ charge carriers/cm$^3$ being performed. Doped silicon layer 5 was porosified by electrochemical etching in an electrolyte containing hydrofluoric acid, having a hydrofluoric acid content in the range of 30 vol. % and having a content of isopropanol or ethanol in the range of 10 vol. % to 30 vol. %, in relation to the total volume of the electrolyte, the current density being 100 mA/cm$^2$. In this case, a porosity of 40% to 50% and a pore diameter of 20 nm were produced. The current preferably flowed through holes 4' in sacrificial layer 3, whereby areas 6' in silicon layer 5 above the recesses were preferentially porosified, as shown in FIG. 2d.

Figure 2E:
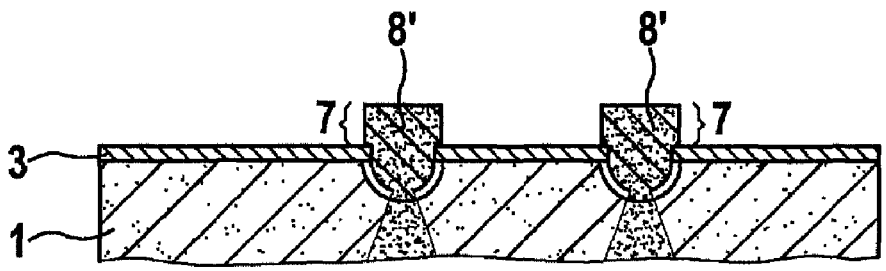

A masking layer, preferably photoresist, was applied to porosified silicon layer 5 and structured by photolithography in a further method step, the masking layer covering the porosified areas of silicon layer 5 above recesses 2'. These areas form a further substructure of porous microstructures 8'. The structures of porous microstructures 8' were etched out of porosified silicon layer 5 by subsequent anisotropic etching, preferably using DRIE methods, as shown in FIG. 2e. The uncovered areas of silicon layer 5 were removed up to the etch stop on silicon oxide sacrificial layer 3, whereby structures 7 of porous microstructures 8' protruding out of sacrificial layer 3 were formed.

Subsequently, sacrificial layer 3 was removed by currentless gas phase etching employing HF vapor. Porous silicon structures 8' were mechanically removed by ultrasound.

Figure 2F:

After the detachment, porous microstructures 8' having a rounded form were obtained, as shown in FIG. 2f.

It may be provided that before the removal of sacrificial layer 3, silicon semiconductor substrate 1 is immersed for a short time in an aqueous KOH solution at a temperature of 80° C., for example, structures 7 of porosified silicon layer 5 protruding from sacrificial layer 3 being rounded by the etching agent. In this way, nearly round porous silicon structures having a diameter of 5 μm, for example, may be obtained.

Silicon wafers are usable as a particularly suitable silicon semiconductor substrate.

As per the example method according to the present invention, recesses are produced in the silicon semiconductor substrate, the recesses each defining a substructure of the porous microstructures.

For this purpose, a first masking layer is applied to the external surface of the front side of a silicon semiconductor substrate and structured, discrete holes having a mean diameter in the range of $\geq 0.1$ μm to $\leq 500$ μm being formed in the first masking layer. In the context of the present invention, the term "hole" means an area of a layer in which the layer has a through opening, which exposes the external surface of the layer lying underneath. For example, the term "hole" means an area of the masking layer in which the masking layer has a through opening, which exposes the external surface of the silicon semiconductor substrate. These holes allow the etching agent access to the silicon semiconductor substrate. In the context of the present invention, the term "discrete" means that the individual holes are not connected to one another. The holes are preferably spaced apart uniformly.

Preferably usable masking materials are $SiO_2$ or $Si_3N_4$ layers. The masking layer may also be implemented from other substances, such as SiC. In the scope of the method according to the present invention, layers applicable using CVD (chemical vapor deposition), for example silicon oxide layers or suitable resist layers, are also usable as the masking layer.

The masking materials, in particular $SiO_2$ or $Si_3N_4$, are preferably structured by photolithography. Photoresist layers having positive or negative exposure properties are preferably usable, which may preferably be structured thereafter using lithographic, in particular photolithographic, methods. For example, liquid resist layers such as photoresist are suitable. Photoresists obtainable under the name AZ® 1529 (AZ Electronic Materials) are usable, for example. The photoresist layer may be exposed using a mask, such as a silicon dioxide layer, and subsequently removed.

The masking layer, in particular a $SiO_2$ or $Si_3N_4$ layer, is preferably etched using suitable etching agents, discrete holes having a mean diameter in the range of $\geq 0.1$ µm to $\leq 500$ µm being formed in the masking layer.

The holes in the masking layer preferably have a round shape. Furthermore, the holes in the masking layer may have a polygonal shape, for example, the holes in the masking layer may be square. The mean diameter of the holes of the masking layer is in the range of $\geq 0.1$ µm to $\leq 100$ µm, more preferably in the range of $\geq 0.1$ µm to $\leq 50$ µm, still more preferably in the range of $\geq 1$ µm to $\leq 10$ µm in preferred specific embodiments.

The recesses in the silicon semiconductor layer may have a round, rounded, or oval shape, for example. Furthermore, the recesses may have a polygonal or pointed shape. In further preferred specific embodiments, the recesses have a pointed shape, for example the form of a polygon such as a tetrahedron. It may be preferable for recesses to taper in depth, run to a point, and/or end in a point. It is advantageous that specific embodiments having pointed recesses may each define a substructure of porous microstructures, which have the form of a microneedle.

In preferred specific embodiments, the recesses have a rounded shape, in particular the form of a semi-sphere or generally the form of a semi-sphere. In advantageous specific embodiments of the method according to the present invention, rounded recesses are produced by isotropic etching. Preferred etching agents for isotropic etching are selected from the group including $ClF_3$, $BrF_3$, $XeF_2$, and/or $SF_6$. Furthermore, other media which isotropically etch silicon, such as mixtures of $HNO_3$ with $H_2O$ and $NH_4F$ and/or mixtures of the above-mentioned etching agents are suitable.

It is advantageous that specific embodiments having rounded recesses, in particular in the form of a semi-sphere or generally the form of a semi-sphere, may each define a substructure of porous microstructures which have a round form. The dimensions of the porous microstructures may thus advantageously be defined during the manufacturing of the microstructures.

In further preferred specific embodiments of the method according to the present invention, pointed or polygonal recesses are produced by anisotropic etching. Preferred anisotropic etching methods are, for example, DRIE (deep reactive ion etching) methods or etching methods employing KOH and/or tetramethyl ammonium hydroxide (TMAH) solutions.

The mean diameter of the produced recesses is in the range of $\geq 0.1$ µm to $\leq 500$ µm, preferably in the range of $\geq 0.1$ µm to $\leq 100$ µm, more preferably in the range of $\geq 1$ µm to $\leq 50$ µm in preferred specific embodiments.

The depth of the recesses may be in the range of several micrometers up to several hundred micrometers, according to the intended use of the microstructures. The depth of the recesses may make up approximately half of the diameter of the recesses in the case of recesses of rounded shape in particular. In other specific embodiments, the depth of the recesses may be in the range of the diameter of the recesses or may be deeper, for example in the range of two to five times the length. This is advantageous in particular if microstructures having a tip are to be produced, for example in the form of microneedles. In preferred specific embodiments of the method according to the present invention, recesses are produced having a depth in the range of $\geq 1$ µm to $\leq 500$ µm, more preferably in the range of $\geq 1$ µm to $\leq 100$ µm, still more preferably in the range of $\geq 1$ µm to $\leq 50$ µm.

In a following method step, a sacrificial layer is applied and structured, the sacrificial layer having discrete through holes having a diameter in the range of $\geq 0.1$ µm to $\leq 150$ µm, which are each situated centrally in the recesses.

The sacrificial layer preferably includes a silicon oxide layer, and the sacrificial layer is preferably implemented from $SiO_2$. For example, a silicon oxide layer may be applied by PECVD (plasma-enhanced chemical vapor deposition) methods. A silicon oxide layer is preferably produced by thermal oxidation. A thermal oxide, which is preferably formed from silicon oxide, may be grown on the silicon semiconductor substrate by thermal oxidation.

The thickness of the sacrificial layer is preferably in the range of $\geq 100$ nm to $\leq 5$ µm, more preferably in the range of $\geq 0.5$ µm to $\leq 4$ µm, particularly preferably in the range of $\geq 0.5$ µm to $\leq 2$ µm.

The sacrificial layer is preferably structured by photolithography. The etching of the sacrificial layer is preferably performed using buffered oxide etching (BOE), preferably employing hydrofluoric acid which is buffered using ammonium fluoride, in particular a $HF/NH_4F/H_2O$ solution. It is advantageous in the case of buffered oxide etching that the sacrificial layer is removable without damaging the silicon layers lying underneath.

In preferred specific embodiments of the method according to the present invention, the discrete through holes of the sacrificial layer have a diameter in the range of $\geq 0.1$ µm to $\leq 100$ µm, preferably in the range of $\geq 0.1$ µm to $\leq 50$ µm, more preferably in the range of $\geq 0.5$ µm to $\leq 50$ µm, still more preferably in the range of $\geq 1$ µm to $\leq 20$ µm, particularly preferably in the range of $\geq 1$ µm to $\leq 10$ µm.

The discrete through holes of the sacrificial layer advantageously allow the current to flow through the holes of the sacrificial layer in a later step of porosification. This provides the advantage that the current may be preferentially conducted to the target structures and they may be preferably etched in a porous manner. A further great advantage which is provided by the holes in the sacrificial layer is that they are filled up by silicon in the further course of the method and may be used as support points and/or predetermined break points of the microstructures on the semiconductor substrate.

In a following method step, silicon is deposited on the sacrificial layer. For this purpose, silicon is deposited in the recesses and a silicon layer is applied. The recesses are preferably completely filled by the deposited silicon. Furthermore, a preferably contiguous silicon layer is applied over it. Both polycrystalline and also monocrystalline layers are suitable, a polycrystalline layer being preferred. A polycrystalline silicon layer may preferably be applied by PECVD (plasma-enhanced chemical vapor deposition) methods. Furthermore, a silicon layer may be applied by PECVD methods, on which an epitactically deposited polycrystalline silicon layer may be applied.

In preferred specific embodiments of the method, a silicon layer having a thickness above the recesses in the range of $\geq 1$ µm to $\leq 100$ µm, preferably in the range of $\geq 2$ µm to $\leq 50$ µm, more preferably in the range of $\geq 5$ µm to $\leq 20$ µm is applied.

The thickness of the silicon layer above the recesses may correspond to the depth of the recesses and/or approximately half of the diameter of the recesses, in particular in the case of microstructures to be manufactured having a round or an essentially round shape. In other specific embodiments, the thickness of the silicon layer may be in the range of the diameter of the recesses or less. This is advantageous in particular if microstructures are to be produced in the form of microneedles.

In preferred specific embodiments of the method, the silicon layer is planarized and/or doped.

In preferred specific embodiments, the silicon layer may be planarized. A preferred method of planarization is polishing. In preferred specific embodiments, the silicon layer may be polished, preferably using CMP (chemical-mechanical polishing), in which the abrasive action of a grained polishing head is supported by the chemical action of a suitable solution. The surface of the microstructure may be defined and shaped in a defined method thereafter by the planarization, in particular polishing, because the topography which results through the application of the silicon layer to the recesses may be leveled by this step.

In further preferred specific embodiments, the silicon layer may be doped. Doping is preferably performed using boron; in particular, boron may be implanted or a boron glass coating may be performed. It may be preferable for the applied silicon layer to be doped. In other specific embodiments, it may be preferable to introduce the doping into the material during the application of the silicon layer.

The pore structure may advantageously be influenced by the selection of the doping. Doping in the range of up to $10^{19}/cm^3$ may be used, the parameter corresponding to the number of doping atoms per $cm^3$ of the silicon semiconductor substrate. A mesoporous structure may be achieved by a doping having $10^{19}/cm^3$, whose pore diameter is preferably in the range of $\geq 2$ nm to $\leq 100$ nm. The advantage of a mesoporous structure of the porosity of the microstructures is in particular that substances or drugs which are to be introduced into a body, for example, may be easily introduced into mesoporous structures.

Preferably, porosification is performed in electrolytes containing hydrofluoric acid, in particular aqueous hydrofluoric acid solutions, or mixtures containing hydrofluoric acid, water, and further reagents, in particular selected from the group including wetting agents such as alcohols, preferably selected from the group including ethanol and/or isopropanol, and/or tension-reducing agents such as surfactants. For example, ethanol and/or isopropanol are usable in the range of $\geq 10$ vol. % to $\leq 30$ vol. %, in relation to the total volume of the electrolyte.

The hydrofluoric acid content of an aqueous hydrofluoric acid solution is preferably in the range of $\geq 10$ vol. % to $\leq 40$ vol. %, in relation to the total volume of the electrolyte. A wetting agent may be added. Preferred wetting agents are selected from the group including isopropanol and/or ethanol.

Preferred current densities are in the range of $\geq 10$ mA/cm$^2$ to $\leq 200$ mA/cm$^2$, preferably in the range between $\geq 50$ mA/cm$^2$ and $\leq 150$ mA/cm$^2$.

A special advantage of the method according to the present invention may be provided in that the current may preferably flow through the holes in the sacrificial layer and is preferentially conducted to the structures to be manufactured. In this way, they are preferably etched to become porous.

The porosity is settable by suitable selection of the processing parameters, such as the electrolyte composition, in particular the hydrofluoric acid concentration, and/or the current density. The porosity specifies the ratio of the empty space inside a structure and the remaining semiconductor substrate or silicon material. A porosity of the porous microstructures in a range of approximately 10% to greater than 90% is thus preferably settable, preferably in the range of $\geq 10\%$ to $\leq 80\%$, particularly preferably in the range of $\geq 20\%$ to $\leq 70\%$.

In preferred specific embodiments of the method, a porosity of the microstructure is set in a range of $\geq 10\%$ to $\leq 90\%$.

"Porosity" is defined in the meaning of the present invention so that it specifies the empty space inside the structure and the remaining substrate material. It may either be optically determined, i.e., from the analysis of microscopic pictures, for example, or chemically. In the case of chemical determination, the following equation applies: porosity $P=(m1-m2)/(m1-m3)$, m1 being the mass of the sample before the porosification, m2 being the mass of the sample after the porosification, and m3 being the mass of the sample after etching using 1 molar sodium hydroxide solution, which chemically dissolves the porous structure. Alternatively, the porous structure may also be dissolved by a KOH/isopropanol solution.

Various pore structures are producible depending on the processing parameters; thus, nanopores, mesopores, or macropores may be generated. The pore size may be set in a range of several nanometers up to 50 nm diameter depending on the hydrofluoric acid concentration, doping, and current density. For example, pores having a diameter $\leq 5$ nm, in the range between $\geq 5$ nm and $\leq 50$ nm, or $\geq 50$ nm may be manufactured. In preferred specific embodiments, pores having a diameter in the range of $\geq 1$ nm to $\leq 1$ µm, preferably in the range of $\geq 2$ nm to $\leq 100$ nm, more preferably in the range of $\geq 5$ nm to $\leq 30$ nm may be manufactured.

In a further method step, a further masking layer is applied and structured on the porosified silicon layer, the further masking layer covering the areas above the recesses, which form a further substructure of the porous microstructures. In this way, the lateral structure of the microparticles to be manufactured may advantageously be formed.

A photoresist layer having positive or negative exposure properties is preferably used for this purpose, which is subsequently preferably structured using photolithographic methods. For example, liquid resist lacquers such as photoresist are suitable. The photoresist layer may be exposed using a mask, such as a chromium layer on a quartz substrate.

The areas above the recesses, which the masking layer covers, preferably have a diameter corresponding to the diameter of the recesses and/or a shape corresponding to the shape of the recesses.

In a further method step, the porosified silicon layer is anisotropically etched. For this purpose, the areas of the porosified silicon layer above the recesses, which are protected by the masking layer, remain. The structures remaining after the etching form a further substructure of the porous microstructures. The sacrificial layer below the porosified silicon layer is not etched by the anisotropic etching. Preferred methods are, in particular, DRIE (deep reactive ion etching) methods. A preferred etching agent is $SF_6$ in this case.

The masking layer may be removed after the etching.

In an optional method step, the areas of the porosified silicon layer above the recesses which are protected by the masking layer, and which form the further substructure of the porous microstructures, may be rounded, preferably by isotropic etching.

In preferred specific embodiments of the method, the substructure of the porous microstructures protruding out of the sacrificial layer is rounded by isotropic etching.

In preferred specific embodiments, the rounding may be performed by brief immersion in a KOH solution and/or a so-called HNA solution including HF, preferably 1 vol. %, $HNO_3$, preferably 3 vol. %, and $CH_3COOH$, preferably 8 vol. %, each in relation to the total volume. A further preferred specific embodiment provides the introduction of the microstructures into an atmosphere containing $ClF_3$. It is advantageous in particular that round or generally round porous silicon microstructures may be manufactured by rounding of the structures above the recesses. However, it may also be advantageous to round the structure in the case of porous microstructures to be manufactured in the form of microneedles.

In a further method step, the sacrificial layer is removed. The removal may preferably be performed by etching in hydrofluoric acid (HF) vapor. This may provide the advantage that the porous microstructures are held by the silicon areas inside the previous holes of the sacrificial layer on the silicon semiconductor substrate. The microstructures may thus be functionalized on the semiconductor substrate in an optional method step.

In other preferred specific embodiments, the removal of the sacrificial layer may be performed by etching in hydrofluoric acid (HF) solution. This may provide the advantage that the porous microstructures may be detached from the silicon semiconductor substrate by the etching. The porous microstructures may be obtained from the solution by filtering, for example.

In further specific embodiments having suitable sacrificial layers, for example a layer system including oxide and silicon-germanium layers, the sacrificial layer may be removed by gas phase etching using etching agents selected, for example, from the group including $ClF_3$ and/or $XeF_2$.

In preferred specific embodiments of the method, the porous microstructures are functionalized before the detachment from the semiconductor substrate. For example, the porous microstructures on the semiconductor substrate may be doped, impregnated, charged, or oxidized before they are detached. The porous microstructures are preferably impregnated with active substances, such as pharmaceuticals. This provides the advantage that uniform and controlled functionalization may be performed on the semiconductor substrate.

The porous microstructures are preferably detached or separated by mechanical action, ultrasound, or by a flow of a compressed gas over them. It is advantageous in this case that the porous microstructures which are held by support points may be detached by slight mechanical action.

It is particularly advantageous in this case that the semiconductor substrate, in particular a silicon wafer, does not have to be completely destroyed in this way, but rather may be reused. For example, the semiconductor substrate may be usable for manufacturing porous microstructures again after grinding and/or polishing. Furthermore, the method according to the present invention is advantageous in that the further usability of the semiconductor substrate allows the manufacturing costs of porous microstructures made of silicon to be reduced.

A further object of the present invention relates to porous microstructures which are manufactured using the method according to the present invention.

The porous microstructures are fundamentally suitable for all applications which require porous microstructures, in particular porous particles or microneedles. In particular, the microstructures are suitable for biological applications, because microstructures made of porous silicon are biocompatible and may be resorbed by the body in particular. In preferred uses of the porous microstructures, they may be used as a reservoir for the application of drugs or active substances or may be used for the manufacture of application units for drugs or medications. It is advantageous that the porous microstructures are usable as a reservoir for drugs or active substances. Furthermore, the porous structures may allow a painless application of drugs or medications.

Furthermore, a use of the porous microstructures manufactured according to the present invention for injection into the bloodstream is advantageous.

A preferred use is a localized application of medications. For example, porous microstructures charged with an angiogenesis inhibitor are suitable for blocking blood vessels which supply a tumor. It is advantageous in this case that the mechanical blocking action may be locally supported by the anti-angiogenic effect through the release of the substance.

For example, usable anti-angiogenic substances are selected from the group including bevacizumab, available under the trade name Avastin® from Genentech/Roche, vandetanib (ZD6474), available under the trade name Zactima® from Astra-Zeneca PLC, and/or the substance PTK787/ZK222584 (Novartis/Schering).

The porous microstructures may have an arbitrary form. The manufactured porous microstructures are preferably round or essentially round or have the form of a microneedle.

A particular advantage of the method according to the present invention may be provided in that round or generally round porous silicon microstructures may be manufactured. In preferred specific embodiments, round or generally round porous silicon microstructures may be manufactured, which have a diameter in the range of $\geq 1$ µm to $\leq 500$ µm, more preferably in the range of $\geq 1$ µm to $\leq 50$ µm, particularly preferably in the range of $\geq 1$ µm to $\leq 5$ µm. These porous silicon microstructures are usable in particular for injection into the bloodstream. It is advantageous in this case that using round porous silicon microstructures having a diameter of less than 5 µm may have the result that vessels are not closed, or are only closed very slightly.

In further preferred specific embodiments, round or generally round porous silicon microstructures may be manufactured, which have a diameter in the range of $\geq 1$ µm to $\leq 500$ µm, more preferably in the range of $\geq 1$ µm to $\leq 50$ µm, particularly preferably in the range of $\geq 10$ µm to $\leq 50$ µm. These porous silicon microstructures may allow vessels to be intentionally closed. Furthermore, an accumulation of the porous silicon microstructures may be achieved. A possible application is an administration of radioactive tracers, for example, which collect in organs and thus allow an examination of the perfusion. A further example application is the targeted suppression of the blood flow, for example, in oncology.

The porous microstructures manufactured by the method according to the present invention preferably have a typical orientation of the pores. The pores which originate from the substrate surface in the porous microstructures are preferably oriented perpendicular to the pores which originate from the recesses.

What is claimed is:

1. A method for manufacturing a porous microstructure in a silicon semiconductor substrate, comprising:
   a) applying and structuring a masking layer on an external surface of a front side of a silicon semiconductor substrate, discrete holes having a mean diameter in the range of $\geq 0.1$ μm to $\leq 500$ μm being formed in the masking layer;
   b) producing recesses in a silicon semiconductor substrate, the recesses each defining a substructure of the porous microstructures;
   c) removing the masking layer;
   d) applying and structuring a sacrificial layer, the sacrificial layer having discrete through holes having a diameter in the range of $\geq 0.1$ μm to $\leq 150$ μm, which are each situated centrally in the recesses;
   e) applying a silicon layer, the silicon layer filling up the recesses and forming a layer above the sacrificial layer;
   f) porosifying the silicon layer;
   g) applying and structuring a further masking layer on the porosified silicon layer, the further masking layer covering areas above the recesses, which form a further substructure of the porous microstructures;
   h) anisotropic etching the porosified silicon layer;
   i) removing the further masking layer;
   j) removing the sacrificial layer; and
   k) detaching or separating the porous microstructures.

2. The method as recited in claim 1, wherein the recesses are rounded recesses, and are produced by isotropic etching.

3. The method as recited in claim 1, wherein the recesses are one of pointed or polygonal recesses, and are produced by anisotropic etching.

4. The method as recited in claim 1, wherein the recesses have a depth in the range of $\geq 1$ μm to $\leq 500$ μm.

5. The method as recited in claim 4, wherein the range is $\geq 1$ μm to $\leq 100$ μm.

6. The method as recited in claim 4, wherein the range is $\geq 1$ μm to $\leq 50$ μm.

7. The method as recited in claim 1, wherein the discrete through holes in the sacrificial layer have a diameter in the range of $\geq 0.1$ μm to $\leq 50$ μm.

8. The method as recited in claim 7, wherein the range is $\geq 1$ μm to $\leq 20$ μm.

9. The method as recited in claim 1, wherein in step e), the silicon layer having a thickness above the recesses in a range of $\geq 1$ μm to $\leq 100$ μm.

10. The method as recited in claim 9, wherein the range is $\geq 2$ μm to $\leq 50$ μm.

11. The method as recited in claim 9, wherein the range is $\geq 5$ μm to $\leq 20$ μm.

12. The method as recited in claim 1, wherein the substructure of the porous microstructures which protrudes from the sacrificial layer is rounded by isotropic etching.

13. The method as recited in claim 1, wherein the silicon layer is at least one of planarized and doped.

14. The method as recited in claim 1, wherein a porosity of the microstructures is set in the range of $\geq 10\%$ to $\leq 90\%$.

15. The method as recited in claim 1, wherein the porous microstructures are functionalized before detachment.

16. Porous microstructures, the porous microstructures being formed in a silicon semiconductor substrate by:
   a) applying and structuring a masking layer on an external surface of a front side of a silicon semiconductor substrate, discrete holes having a mean diameter in the range of $\geq 0.1$ μm to $\leq 500$ μm being formed in the masking layer;
   b) producing recesses in a silicon semiconductor substrate, the recesses each defining a substructure of the porous microstructures;
   c) removing the masking layer;
   d) applying and structuring a sacrificial layer, the sacrificial layer having discrete through holes having a diameter in the range of $\geq 0.1$ μm to $\leq 150$ μm, which are each situated centrally in the recesses;
   e) applying a silicon layer, the silicon layer filling up the recesses and forming a layer above the sacrificial layer;
   f) porosifying the silicon layer;
   g) applying and structuring a further masking layer on the porosified silicon layer, the further masking layer covering areas above the recesses, which form a further substructure of the porous microstructures;
   h) anisotropic etching the porosified silicon layer;
   i) removing the further masking layer;
   j) removing the sacrificial layer; and
   k) detaching or separating the porous microstructures.

17. A method of applying drugs, comprising:
manufacturing a porous microstructure in a silicon semiconductor substrate, including:
   a) applying and structuring a masking layer on an external surface of a front side of a silicon semiconductor substrate, discrete holes having a mean diameter in the range of $\geq 0.1$ μm to $\leq 500$ μm being formed in the masking layer,
   b) producing recesses in a silicon semiconductor substrate, the recesses each defining a substructure of the porous microstructures,
   c) removing the masking layer,
   d) applying and structuring a sacrificial layer, the sacrificial layer having discrete through holes having a diameter in the range of $>0.1$ um to $<150$ um, which are each situated centrally in the recesses,
   e) applying a silicon layer, the silicon layer filling up the recesses and forming a layer above the sacrificial layer,
   f) porosifying the silicon layer,
   g) applying and structuring a further masking layer on the porosified silicon layer, the further masking layer covering areas above the recesses, which form a further substructure of the porous microstructures,
   h) anisotropic etching the porosified silicon layer,
   i) removing the further masking layer,
   j) removing the sacrificial layer, and
   k) detaching or separating the porous microstructures, and
applying drugs using the porous microstructure.

* * * * *

UNITED STATES PATENT AND TRADEMARK OFFICE
CERTIFICATE OF CORRECTION

PATENT NO.       : 8,377,315 B2
APPLICATION NO. : 12/810973
DATED            : February 19, 2013
INVENTOR(S)      : Scholten et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 405 days.

Signed and Sealed this

First Day of September, 2015

Michelle K. Lee
*Director of the United States Patent and Trademark Office*